United States Patent [19]

Altemark et al.

[11] Patent Number: 4,941,345
[45] Date of Patent: Jul. 17, 1990

[54] METHOD AND APPARATUS FOR THE MEASUREMENT OF GAS PROPERTIES

[75] Inventors: Detlef Altemark, Dorsten; Robert Hess, Essen; Karl H. Hillringhaus, Bottrop, all of Fed. Rep. of Germany

[73] Assignee: Ruhrgas Aktiengesellschaft, Essen, Fed. Rep. of Germany

[21] Appl. No.: 188,395

[22] PCT Filed: Jul. 13, 1987

[86] PCT No.: PCT/EP87/00377
  § 371 Date: Mar. 14, 1988
  § 102(e) Date: Mar. 14, 1988

[87] PCT Pub. No.: WO88/00693
  PCT Pub. Date: Jan. 28, 1988

[30] Foreign Application Priority Data

Jul. 14, 1986 [DE] Fed. Rep. of Germany ....... 3623664

[51] Int. Cl.$^5$ ............................................. G01N 9/32
[52] U.S. Cl. ................................... 73/23.2; 73/30.01; 73/31.04
[58] Field of Search ............... 73/30, 23, 54, 32 R, 73/55, 56

[56] References Cited

U.S. PATENT DOCUMENTS

| | | | |
|---|---|---|---|
| 1,958,878 | 5/1934 | Albersheim et al. | 73/55 |
| 2,777,320 | 1/1957 | Boulestreau | 73/30 |
| 2,783,641 | 5/1957 | Smith | 73/30 |
| 3,081,621 | 3/1963 | de Bruyne | 73/55 |

FOREIGN PATENT DOCUMENTS

| | | |
|---|---|---|
| 0022493 | 1/1981 | European Pat. Off. |
| 0151486 | 8/1985 | European Pat. Off. |
| 3237130 | 4/1984 | Fed. Rep. of Germany |

OTHER PUBLICATIONS

Madhavan et al., The Review of Scientific Instruments, vol. 40, No. 10, 10/69, pp. 1293–1294.

Primary Examiner—Hezron E. Williams
Attorney, Agent, or Firm—Spensley Horn Jubas & Lubitz

[57] ABSTRACT

A method and apparatus for the measurement of the properties of fuel gases dependent upon flow and pressure, and more particularly upon the dyanmic viscosity and/or the density of the fuel gases. The apparatus includes a device to control the flow of the fuel gas and at least one flow restrictor in the gasway. The design and the operation of such an apparatus is simplified by the integration of a gas holding device having a capacity which changes in response to the pressure difference between the pressure inside the inner chamber of the device and the ambient pressure. An aneroid capsule element in a line connecting a closeable gas inlet and at least one flow restrictor may be used for this purpose. A time measurement device may be switched on and off as a function of predetermined capacities of the gas holding device.

14 Claims, 3 Drawing Sheets

METHOD AND APPARATUS FOR THE MEASUREMENT OF GAS PROPERTIES

BACKGROUND OF THE INVENTION

1. Field of the Invention

The present invention relates to a method of and an apparatus for the measurement of gas properties which may be determined from a volume flow rate and/or a pressure difference such as the dynamic viscosity and the density of fuel gases using a device to control the flow of the gas so measured and at least one flow restrictor.

2. Description of Related Art

A method of and an apparatus for the flameless measurement and/or control of heat input into gas appliances of a similar nature are known from the European Patent Application No. 0 022 493. Said application reveals a method of and an apparatus for the measurement of the dynamic viscosity and the density of fuel gases and of other fuel gas properties such as the higher heating value, the lower heating value or the Wobbe index. According to the teachings of said application, at least part of the gas to be analyzed is passed through a laminar flow restrictor taking the form of a capillary tube for dynamic viscosity measurement and through a turbulent flow restrictor taking the form of an orifice plate for density measurement. Said application further proposes a series connection of said laminar flow restrictor and said turbulent flow restrictor for the purpose of measuring both dynamic viscosity and the density of a fuel gas for determining the higher or the lower heating value of said gas. To determine said dynamic viscosity and said density, it is necessary to obtain at least two measured values namely the pressure difference across the appropriate flow restrictor and the volume rate of flow expressed in terms of volume per time of the gas passing across said flow restrictor. The measurements proposed by said application are made continuously, as the gas to be measured continues to flow, determining the upstream and the downstream flow restrictor pressures, thence a total of five values having to be measured and to be combined for obtaining the dynamic viscosity and the density of the gas being measured. The gas so flowing continuously must for the purposes of the application of said method further be discharged into a main gas line or into a line taking said gas to a gas-fired appliance or gas-fired equipment. It is an object of the present invention to simplify the method of measurement and the measurement apparatus of the kind indicated above.

SUMMARY OF THE INVENTION

For said purpose the method according to the present invention is characterized by the following steps: providing a gas holding device having a chamber said chamber having a capacity that is subject to changes in response to pressure differences between the interior of said chamber and the ambient atmosphere; determining said response; thereafter filling said chamber with the gas to be examined thereby increasing said chamber capacity; then interrupting the gas supply into said chamber and permitting the gas in said chamber to discharge across said at least one flow restrictor while measuring a time period $\Delta t$ required for a change in the capacity of said chamber between two pre-determined capacities or between predetermined pressure differences $\Delta p$; and determining said gas property from said measured time interval $\Delta t$ and from said change in capacity respectively from a change in said pressure difference $\Delta p(t)$ associated with said change in capacity. The apparatus proposed by the present invention is characterized by a gas holding device comprising a chamber said chamber having a capacity changing in response to the pressure difference between the pressures in side and outside said chamber, said chamber being adapted to be filled across a closable gas inlet and being connected with at least one flow restrictor element and a time measurement device adapted to be switched on and off as a function of pre-determined capacities of said gas holding device or pre-determined pressure differences.

The present invention thereby enables the measurement of the density, of the dynamic viscosity and of certain other correlating properties of gases and more particularly fuel gases to be reduced to a simple time measurement. To this effect neither an elaborate system for keeping the volume rate of flow or the pressure differences across flow restrictors constant nor further measured values are required. Of course, the thermodynamic state variables of pressure and temperature may be measured for desirable correlations. It is an advantage of the present invention that the size of the measurement apparatus may be kept relatively small and that only small volumes of gas of an order of several cubic centimeters are necessary, allowing measurement times of less than one second and eliminating the need for returning the gas tapped for the measurement into the main gas line.

It is thence a principle of the present invention to make a discontinuous measurement, to integrate appropriate flow restrictors downstream of a volume flow rate dosing device, to measure the time required for a given gas volume to pass each such flow restrictor and to compute the property to be measured from the time so measured and the characteristic curve of the volume flow rate dosing element previously determined by calibration.

In a preferred embodiment of the present invention the gas holding device referred to hereinabove acting as said volume flow rate dosing element is a so-called aneroid capsule which is characterized by an elasto-mechanical behavior of a particularly good reproducibility and the exact and problem-free correlation of changes in volume and pressure differences with a given volume rate of flow V.

In other embodiments of the present invention, said gas holding device may be spring-loaded bellows, a spring-loaded piston/cylinder device or another expansion vessel, always provided that the change in capacity of said gas holding device may be measured by an appropriate displacement measuring device or that change in pressure difference between the inner chamber of said device and the ambient pressure may be correlated with a certain volume rate of flow.

To substantially enhance the accuracy both of the density and of the viscosity measured using the method proposed by the present invention, the gas to be measured discharged from the gas holding device may, during different measurement intervals, be passed to a density-sensing device (orifice plate) and a viscosity-sensing device (capillary tube) and values representative of the density and the viscosity of said gas may be measured, a limited influence of viscosity on said density-sensing device and a limited influence of density on said viscosity-sensing device being tolerated and the errors of the values so measured resulting from said influences may be corrected for by computational means. If such a correction is made it is unnecessary to design said density-sensing device which is preferably an orifice plate in such a manner that a selective density measurement is made using said orifice plate. It is then equally unnecessary to design said viscosity-sensing device which may be a capillary tube in such a manner that viscosity is selectively measured, thus allowing, for example, the use of a relatively short capillary tube. Microprocessor and storage devices usually employed for methods of measurement and measuring apparatus of the kind divulged herein make it possible to obtain very accurate measured values and to substantially eliminate systematic errors.

A computational correction of the kind referred hereinabove is preferably made by iteration. For the purposes of said iteration, each value so measured is used as a first approximation for a first iterative step and the improved approximation resulting from said first iterative step is used as a corrected approximation for a second iterative step and the iterations are continued until the relative difference between the values obtained by two successive iterative steps (N and N−1) is smaller than a pre-determined and stored maximum difference.

Further claims describe useful other embodiments of the present invention mainly to warranting an accurate and automatically repeatable measurement and measured value processing operation.

With regard to size, shape, material and design as well as operating conditions, the components, elements and devices as well as the steps described hereinabove for the application of the present invention are not subject to any particular restrictions, thence allowing the unrestricted use of known selection criteria for the specific field of application of the present invention.

BRIEF DESCRIPTION OF THE DRAWINGS

Further details, characteristics and advantages of the present invention are revealed in the description of the accompanying drawings presenting a preferred embodiment of the measurement apparatus revealed by the present invention, wherein.

DESCRIPTION OF THE PREFERRED EMBODIMENTS

Figure 1:
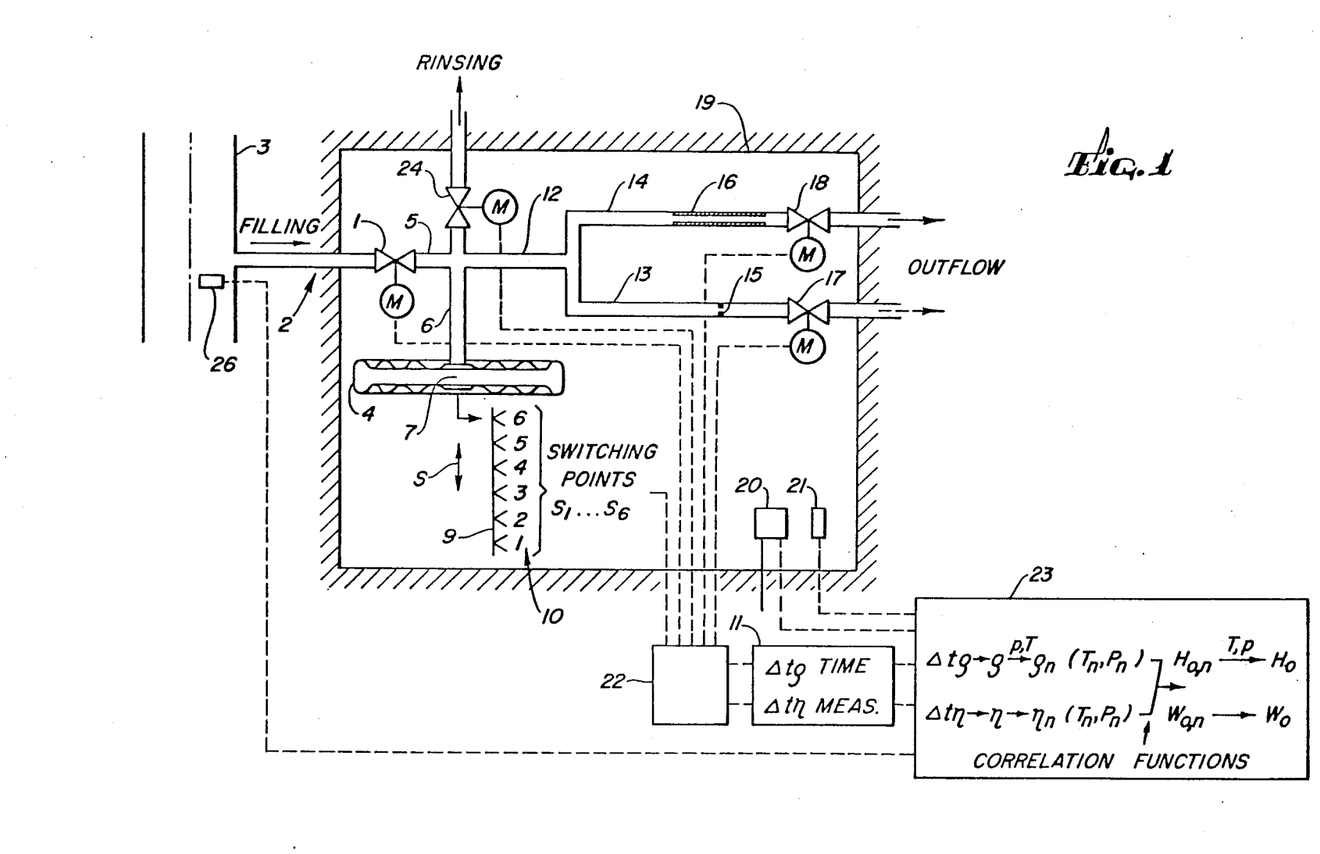
FIG. 1 is a schematic of a measurement apparatus for measuring the density and the dynamic viscosity and correlating properties of a gas.

The measurement apparatus depicted in FIG. 1 comprises a gas inlet (2) consisting of a gas supply line branching off a main gas line (3). Said gas inlet is closable by a valve (1). Said closable gas inlet (2) is connected by fluid-carrying lines (5, 6) with a gas holding device (4), said gas holding device being an aneroid capsule.

Said aneroid capsule is characterized by a pressure difference-versus-displacement behaviour of excellent reproducibility: the expansion (lift s) of said aneroid capsule is exactly correlated with the pressure difference $\Delta p$ between the pressure inside the inner chamber (7) of said aneroid capsule and the ambient pressure outside said aneroid capsule; said lift s is hence a one-to-one function of said pressure difference $\Delta p$. As said correlation exists, the measurement of the difference between the pressure inside said inner chamber (7) of said gas holding device (4) (aneroid capsule) and the ambient pressure may be replaced by a measurement of said lift s, using the value of said lift s in the absence of any such pressure difference as a reference. Said aneroid capsule (4) consists of a flat, closed vessel, usually metallic, the circular bottom and top surfaces whereof are corrugated diaphragms. Gas enters the inner chamber (7) of said aneroid capsule preferably through one stationary connection arranged in the center of one of the capsule diaphragms from a line (6) serving as a feeder and discharge line, thereby achieving a maximum lift s of a lift index element (8) along a stationary lift scale (9), said lift index element (8) being situated opposite said stationary line (6). Such a readable mechanical lift index element may be replaced by an electric, an optical or any other lift pick-up device. For pre-settable lifts $s_1$, $s_2$, etc., said lift scale (9) is provided with switching points (10) so that a time measurement by an associated time measurement device (11) is triggered or stopped, as said lift index element (8) reaches said switching points.

The gas holding device (4) is connected with two flow restrictors (15, 16) by the fluid-carrying line (6), a downstream fluid-carrying line (12) and fluid-carrying lines (13 and 14) branching off said line (12). Downstream of said flow restrictors, the measuring apparatus further comprises valves (17, 18) preferably isolating valves serving as closable gas outlets which pass the gas to be measured without any substantial pressure drop, thereby allowing an expansion to ambient pressure directly downstream of said flow restrictors. In the embodiment of the present invention depicted in FIG. 1, the gas holding device (4), the lines (5), (6), (12), (13) and (14), the flow restrictors (15), (16) and the valves (1), (17), (18) are arranged inside a thermostated casing (19). A temperature-sensing device (20) situated inside said casing (19) is provided for temperature control or if no thermostatic temperature control is used for computational temperature correction. A pressure pick-up (21) arranged inside said casing (19) in the immediate vicinity of said temperature-sensing device (20) measures the ambient pressure outside the gas holding device (4) and allows a computational pressure correction as the measured value is being processed. The flow restrictor (16) (laminar flow restrictor) is a capillary tube of known geometry, for which it is known that the dynamic viscosity is proportional to the pressure drop $p_1$ across said capillary tube and inversely proportional to the volume rate of flow V through said capillary tube, if flow is laminar (Hagen-Poiseuille Law).

$$\eta \sim \frac{\Delta p_e}{V} \tag{1}$$

The second flow restrictor (15) (turbulent flow restrictor) is a thin-walled orifice plate, but, in lieu of such an orifice plate, another turbulent flow-restricting device may be used for which for a limited Reynolds number range the density is proportional to the pressure drop $\Delta p_t$ and inversely proportional to the square volume rate of flow $\dot{V}^2$ (Conservation of Energy Law).

$$\rho \sim \frac{\Delta p_t}{\dot{V}^2} \quad (2)$$

To determine $\Delta p_1$ and $\dot{V}$ on the one hand and $\Delta p_t$ and $\dot{V}$ on the other hand, the present invention proposes the exclusive measurement of the time required for a certain volume of gas held in gas holding device (4) to be discharged from said gas holding device (4) across either flow restrictor (15) or flow restrictor (16) with valve (1) being closed. Said volume is defined by the lift s between two switching points (10). Such a method may be applied since, for gas holding device (4), a one-to-one correlation exists between the capacity V of said gas holding device (4) and the pressure difference $\Delta p$ between the pressure inside the inner chamber (7) of said gas holding device (4) and the ambient pressure V ($\Delta p$). For the gas holding device incorporated in the measurement apparatus, said correlation is determined by calibration using a suitable calibration gas of known properties and stored preferably in computing means such as a microprocessor prior to the commencement of the measurement cycle.

The correlation V (p) allows the determination of the change in the capacity of said gas holding device as a function of time, equivalent to the volume rate of flow $\dot{V}$ $$\dot{V} = \frac{dV}{d\Delta p} \cdot \frac{d\Delta p}{dt}, \quad (3)$$

wherein dV/dp is a function derived from the above-described caracteristic curve of the gas holding device, said function having a specific value for a specific design of the gas holding device.

As equations (1) and (3) as well as equations (2) and (3) demonstrate, the change in pressure difference as a function of time $\Delta p(t)$ is exclusively determined by the dynamic viscosity of the fluid (if a laminar flow restrictor is used) or the density of the fluid (if a turbulent flow restrictor is used).

Figure 3:
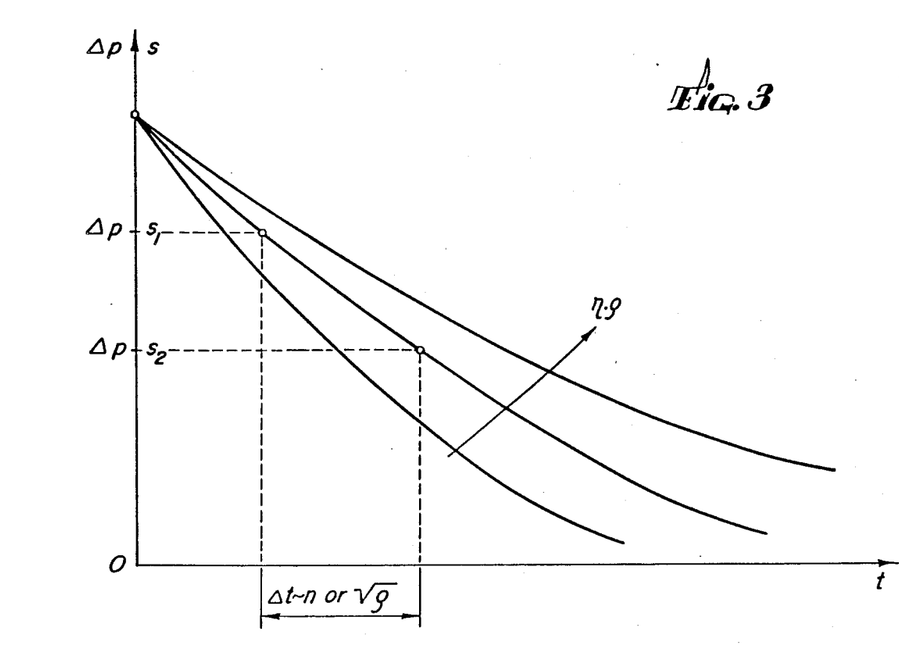
FIG. 3 is a similar displacement-versus-time diagram showing the time behavior of an aneroid capsule incorporated in the apparatus depicted in FIG. 1 using said aneroid capsule as a gas holding device for different gases.

FIG. 3 is a qualitative plot of the change in the pressure difference $\Delta p$ as a function of time, using dynamic viscosity and density as parameters, assuming that gas is discharged continuously from the full gas holding device across flow restrictor (15) or (16) in response to the spring-like elastic behavior of said gas holding device, the time difference $\Delta t$ for gas discharge between two pre-determined lift markings $s_1$ and $s_2$ (equivalent to differential pressures $\Delta p_1$ and $\Delta p_2$, being a measure of the dynamic viscosity or the square root of the density of the gas being measured. For measurement to be as accurate as possible, the switching points between which time is measured are selected in such a manner that the $\Delta p(t)$ curve between said two switching points is substantially linear.

If, to determine the higher heating value $H_o$ of a gas, both the dynamic viscosity and the density of said gas are to be measured, then, according to the teachings of the present invention, both flow restrictors (15) and (16) are exposed to the gas to be measured during one cycle or discharge operation during two different subsequent time intervals, the density being preferably determined first and the dynamic viscosity thereafter. The density is thus measured when the pressure difference is relatively high, thereby minimizing the change in the Reynolds number during the density measurement, whereas the dynamic viscosity is measured when the Reynolds number is relatively low and the pressure difference is thence relatively small. The measurement of both the dynamic viscosity and the density during one discharge operation ensures that both properties are measured for the same gas stored prior to said measurement in the gas holding device (4).

The density and the dynamic viscosity so obtained may then be used to determine dependent variables, such as the higher heating value $H_o$ of a gas, using a correlation function, such as $H_o$ ($\eta,\rho$), as described in more detail in the European Patent Application No. 0 022 493, the measurement of the dynamic viscosity being sufficient for a first approximation of the Wobbe index $W_0$.

To determine, in addition to $\eta$, $\rho$, $H_o$ and $W_o$ at reference conditions, $\eta$, $\rho$, $H_o$ and $W_o$ at flowing conditions it is necessary also to measure the temperature (T) and the pressure (p) of the sample gas at the point at which said gas is tapped (temperature and pressure pick-ups (26) in gas line (3) in order to be able to make the desired conversion.

To enhance the accuracy of the measurement, the apparatus may be calibrated using a calibration gas, such as $CH_4$, at more or less frequent time intervals depending on calibration requirements.

The pressure to which the gas holding device is filled may be limited by appropriately opening and closing valve (1). Said opening and closing operation may be implemented using an appropriately selected switching point—point $s_1$ in FIGS. 1 and 2—at lift marking (9) and a control unit (22). Said control unit may be provided for controlling all valves, the time measurement device (11) and a computing device (23) in association with lift s of gas holding device (4) and switching points (10). Said control unit (22) may be integrated in a computing device (23), as may be time measurement device (11).

As gas holding device (4) is being filled, the flow restrictors (15 and 16) are also exposed to the fluid pressure to accelerate the measurement. Said pressure—and hence the pressure difference dependent thereupon—should be as low as possible, for example, several mbar (hPa) to eliminate compressibility influences during the discharging operation and to keep the Reynolds number low.

Finally, switching points (10) should be selected in such a manner that the time for which flow across each of the two flow restrictors is measured is approximately equal to the time for which flow across the other flow restrictor is measured, thereby giving equal weight to the accuracy of time measurement both for density and for dynamic viscosity determination.

Figure 2:
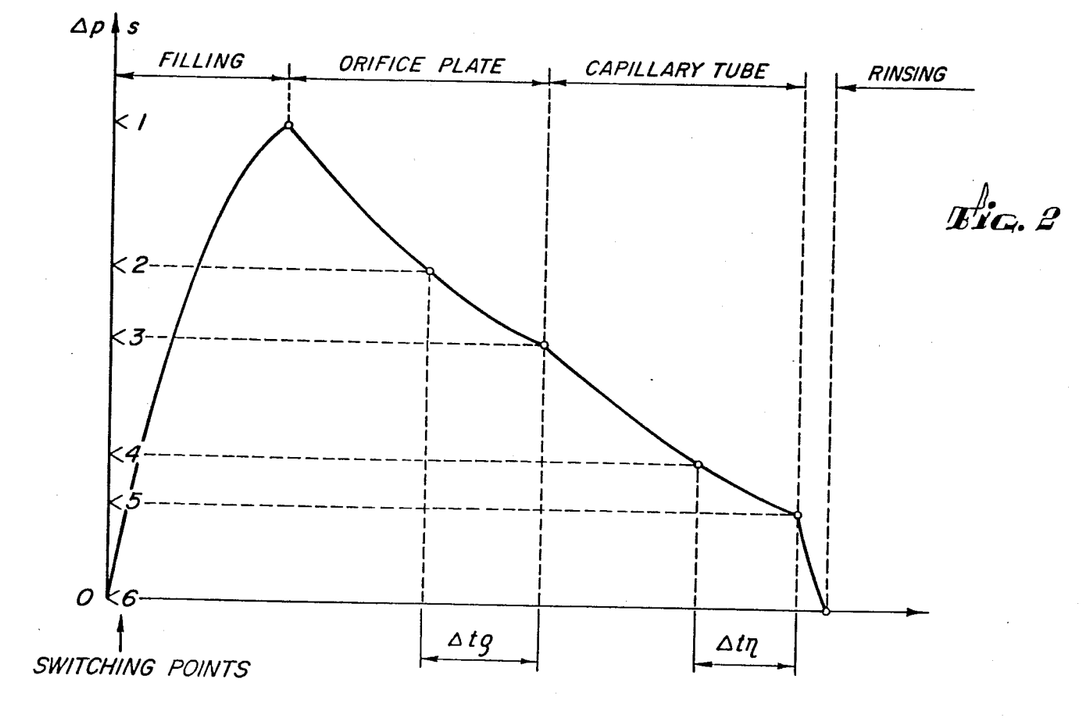
FIG. 2 is a displacement-versus-time diagram for one complete measurement cycle of the apparatus depicted in FIG. 1 showing when the time measurement device of said apparatus is switched.

Switching points (10) should also be selected in such a manner that gas flow across the flow restrictors will be quasi-stationary prior to the time measurement being triggered as shown in more detail in FIG. 2, the run-up times thence not being measured because the method divulged herein is a discontinuous method providing for the measurement of the properties of a defined volume of gas during each cycle.

The method proposed by the present invention for the measurement of gas properties and the operation of the measurement apparatus shown in FIG. 1 will now be described by reference to FIG. 2. Prior to the commencement at least of the first cycle of measurement, said measurement apparatus and more particularly the characteristic curve of the gas holding device (4) embodied by an aneroid capsule must be calibrated and determined by a calibration gas of known properties, appropriate calibration data having been or being stored in computing means (23). Upon the commencement of each operating cycle, mainly the gas holding device (4) should be substantially free from residual gases from preceding operating cycles such as sample calibration or purge gases. It is therefore useful to minimize the distance between the diaphragms of the aneroid capsule (4) in order to keep the size of the inner chamber (7) as small as possible and to minimize the capacity of line 6 by keeping its length as short as possible. As the measurement cycle commences, the pressure difference is substantially zero. When valve (1) has been opened, the sample gas enters the measurement apparatus through inlet (2) and the pressure rises until a specified filling pressure level is reached, the gas holding device having been expanded so that the lift index element (8) has reached switching point $s_1$, valve (17) and (18) associated with flow restrictors (15) and (16) and valve (24) being either closed for rapid pressure build-up in gas holding device (4) or at least partially opened for purging. When said switching point $s_1$ has been reached at least inlet valve (1) is closed (if previously opened, valves (18) and (24) are also closed) and valve (17) is opened to discharge the gas trapped in the measurement apparatus and in particular in the gas holding device (4) across line (13) and flow restrictor (15) until the lift index element (8) has reached switching point (3). As indicated in FIG. 2, time measurement commences when lift index element (8) reaches switching point $s_2$ and ends when lift index element (8) reaches switching point $s_3$. As switching point $s_3$ is reached, valve (17) is closed and valve (18) is opened to discharge the sample gas thereupon through capillary tube (16) and valve (18). Upon reaching switching point $s_4$ time measurement commences (for the measurement of dynamic viscosity) and stops upon reaching switching point $s_5$. During the run-up times between switching points $s_1$ and $s_2$ and switching points $s_3$ and $s_4$, flow becomes quasi-stationary as required for the measurements between switching points $s_2$ and $s_3$ and switching points $s_4$ and $s_5$. Upon reaching switching point $s_5$, valve (18) is closed and valve (24) is opened, so that the gas holding device (4) pressure difference decays to zero prior to the commencement of a new measurement cycle at switching point $s_6$.

For the measurement of density and viscosity by the method divulged hereinbefore, it is not necessary for the orifice plate (15) and capillary tube (16) serving as sensing devices to be designed in such a manner that the orifice plate will selectively measure density and the capillary tube will selectively measure viscosity. A certain limited influence of density on the measured viscosity and of viscosity on the measured density may rather be tolerated. The resulting systematic error may be corrected for by means of the computing device or processor (22) using preferably iterative techniques. Such a correction allows a simplification of the design of the appropriate sensing device (15) and (16) thereby reducing the necessary size of the measurement apparatus. Such a correction for such a systematic error may be made with any desired precision using such an iterative technique, as iteration by the computer after the measurement cycle will continue until the relative difference between two iterated results has disappeared for practical purposes.

For the purpose of correcting the systematic error of the measured density, a characteristic $\alpha(Re)$ function is inputted into the storage means associated with computing device (22), $\alpha$ being the flow coefficient and Re being the Reynolds number. Said Reynolds number is given by:

$$Re = \frac{\rho \cdot C \cdot L}{\eta} \quad (4)$$

where C is the characteristic velocity of flow and L is the characteristic orifice plate dimension.

For orifice plate, $$C \sim \alpha \sqrt{\frac{\Delta p}{\rho}} \quad (5)$$

Thence, $$Re = \frac{\alpha \sqrt{\rho} \cdot \sqrt{\Delta p} \cdot L}{\eta} \quad (6)$$

For calibration using a calibration gas such as $CH_4$ under laboratory conditions, the pressure difference ratio and the characteristic orifice plate dimension ratio being unity, $$\frac{Re}{Re_{CH4}} = \frac{\alpha}{\alpha_{CH4}} \sqrt{\frac{\rho}{\rho_{CH4}}} \cdot \frac{\eta_{CH4}}{\eta} \quad (7)$$

In a first iterative step using the measured $\rho/\rho_{CH4}$ and $\eta/\eta_{CH4}$ values and a first approximation of $\alpha/\alpha_{CH4}=1$, a first approximation of $Re/Re_{CH4}$ may be determined. For a known characteristic orifice plate curve stored in the storage means of computing device, $\alpha/\alpha_{CH4}=f(Re/Re_{CH4})$ may be used to determine a new approximation of $\alpha/\alpha_{CH4}$. In a first iterative step (1), $\rho/\rho_{CH4}$ is corrected by $$\left(\frac{\rho}{\rho_{CH4}}\right)_{(1)} = \left(\frac{\alpha}{\alpha_{CH4}}\right)^2_{(1)} \cdot \left(\frac{\rho}{\rho_{CH4}}\right)_{(o)} \quad (8)$$

where $\rho/\rho_{CH4(o)}$ is the measured value and $\rho/\rho_{CH4(1)}$ is the corrected measured value after said first iterative step. Said corrected value may be used in a second iterative step for the determination of second approximations of $Re/Re_{CH4}$, $\alpha/\alpha_{CH4}$ and $\rho/\rho_{CH4}$. Iteration for the elimination of the systematic error attributable to the flow coefficient $\alpha$ is continued as described hereinabove until the relative difference between the results of iterative step (N−1) and the next succeeding iterative step (N) is less than a maximum relative difference stored in the computing device or its associated storage element, thereby eliminating the need for designing the orifice plate for maintaining an exactly constant flow coefficient $\alpha$ over a wide Reynolds number range and allowing the toleration of a limited viscosity influence, the resulting systematic error being corrected for by the iterative technique described hereinbefore.

The measured variables $\rho$ and $\eta$ may also be used for an iterative correction for the error attributable to the influence of $\rho$ on flow through the capillary tube.

Flow through such a capillary tube is only described sufficiently accurately by the Hagen-Poiseuille law if other influences and more particularly the influence of density on said flow are comparatively limited. Such influences occur as a result of flow patterns at the inlet and at the outlet of such a capillary tube. At said inlet, a pressure difference occurs to accelerate flow to the velocity of flow in the narrow cross-section of the capillary tube and a somewhat larger pressure difference is also necessary for the formation of a parabolic-shape laminar flow profile. Said pressure differences are usually not made up for at the outlet end of a capillary tube. Apart from the geometry of the capillary tube, the density of the gas is the only factor influencing said pressure differences. According to published sources, the density-dependent inlet pressure difference:

$$\Delta p_\rho = (1 + 1{,}15)\frac{\rho}{2} \cdot \left(\frac{\dot{V}}{A}\right)^2 \tag{9}$$

According to the Hagen-Poiseuille law, the viscosity-dependent pressure difference across a circular cross-section capillary tube is given by $$\Delta P\eta = 32 \cdot (l \cdot \eta / d^2)(\dot{V}/A) \tag{10}$$

For the correlation $\eta \sim \Delta p / \dot{V}$ desirable for viscosity measurement to apply, as the total pressure drop across the capillary tube is given by $$\Delta P = \Delta P\rho + \Delta P\eta \tag{11},$$

$\Delta P\rho \ll \Delta P\eta$. Said condition is fulfilled, as $$\frac{\Delta p_\rho}{\Delta p_\eta} = \frac{2{,}15 \cdot \frac{\rho}{2} \cdot \left(\frac{\dot{V}}{A}\right)^2}{32 \cdot \frac{l \cdot \eta}{d^2} \cdot \frac{\dot{V}}{A}} \ll 1 \tag{12}$$

From equation (10), $$\frac{\dot{V}}{A} = \frac{\Delta p_\eta}{32 \cdot \frac{l \cdot \eta}{d^2}} \tag{13}$$

For an iterative correction for the influence of density on the measured viscosity, the following initial values are used for the iterative calculations:

$\rho$, as determined during the immediately preceding density determination $\eta^{(o)}$ as determined by the immediately preceding measurement, no correction having been made for the influence of density $\Delta P\eta^{(o)} = \Delta P$ = being the average pressure difference during one cycle (constant for aneroid capsule)

For $N \geq 1$ iterations, the following method is applied during each iterative step:

$$\Delta p_\rho^{(N)} = 2{,}15 \cdot \frac{\rho}{2} \left(\frac{\Delta p_\eta^{(N-1)}}{32\frac{L}{d^2} \cdot \eta^{(N-1)}}\right)^2 \tag{1}$$

$$\Delta p_\eta^{(N)} = \Delta p - \Delta p_\rho^{(N)} \tag{2}$$

$$\eta^{(N)} = \eta^{(N-1)} \cdot \frac{\Delta p_\eta^{(N)}}{\Delta p_\eta^{(N-1)}} \tag{3}$$

The above iteration is continued until the relative $\eta$ difference given by $$\frac{\eta^{(N)} - \eta^{(N-1)}}{\eta^{(N)}} = \epsilon_\eta$$

is less than a predetermined maximum difference Eg.

As mentioned hereinabove, the measured density, the measured viscosity, the initial values required for the iterations and the results of the iterations are stored in a storage device not shown in FIG. 1 but associated with computing device (22).

For practical purposes, the calibration referred to hereinabove may be made by adjusting the measuring apparatus to certain reference time intervals for the time measurement intervals between the above-mentioned switching points $s_2$ and $s_3$ as well as $s_4$ and $s_5$ using a calibration gas of known properties. In the measuring cycles following such a calibration, the actual times measured between said switching points are then a measure of the gas properties to be determined.

All valves of the measuring apparatus and in particular valves (17) and (18) should of the rapid closing and the rapid opening type in order to avoid or to minimize dead times. Said valves and their actuators should operate without the dissipation of heat and should provide a tight seal when closed in order to avoid an influence of leaks across closed valves on the measured variables. All valves are of the low vibration kind in order to avoid any influence of vibrations on the characteristic aneroid capsule curve. The materials of the components of the measuring apparatus depicted in FIG. 1 which are exposed to the test gas are selected in such a manner that they will not absorb the gases to be measured.

The time measurement which is made according to the teachings of the present invention to determine gas properties provides an excellent resolution if compared with other methods of measuring said properties.

I claim:

1. A method for measuring a gas property, the method comprising the steps of:
   providing a gas holding chamber having a volume that varies in response to pressure differences between the interior of the chamber and the ambient atmosphere;
   determining the correspondence between variations in the volume of the gas holding chamber and pressure differences between the interior of the chamber and the ambient atmosphere;
   supplying gas to the chamber, whereby the pressure difference between the interior of the chamber and the ambient atmosphere is increased and the volume of the chamber is increased;
   interrupting the gas supply to the chamber;

permitting the gas in the chamber to discharge across at least one flow restrictor, whereby the pressure difference between the interior of the chamber and the ambient atmosphere is decreased and the volume of the chamber is decreased;

measuring the period of time taken for the volume of the chamber to decrease from a first predetermined volume representative of a first pressure difference to a second predetermined volume representative of a second pressure difference; and determining a resulting volume rate of flow and a gas property from the measured time period and from the decrease in volume.

2. A method according to claim 1 wherein the gas holding chamber is an aneroid capsule.

3. A method according to claim 1 wherein the change in the pressure difference during the measured time period is a substantially linear function of time.

4. A method according to claim 1 further comprising the step of permitting the gas in the chamber to discharge across a first flow restrictor and a second flow restrictor.

5. A method according to claim 4 wherein the first flow restrictor is a turbulent flow restrictor and the second flow restrictor is a laminar flow restrictor.

6. A method according to claim 1 further comprising the step of interrupting the flow of gas to the gas holding chamber at a predetermined filling pressure inside the gas holding chamber.

7. A method according to claim 1 further comprising the step of exposing the at least one flow restrictor to the gas flowing into the gas holding chamber as the gas holding chamber is being supplied with gas.

8. A method according to claim 1 further comprising the step of limiting the pressure inside the gas holding chamber to a maximum pressure of approximately 100 nbar to thereby limit the effect of the compressibility of the gas.

9. A method according to claim 1 wherein the step of measuring the time period is commenced when the flow of gas across the at least one flow restrictor becomes quasi-stationary.

10. A method according to claim 1 further comprising the steps of:
directing gas discharged from the gas holding device to a density sensing device during a first measurement interval,
directing gas discharged from the gas holding device to a viscosity sensing device during a second measurement interval,
measuring a density value representative of the density of the gas,
measuring a viscosity value representative of the viscosity of the gas,
measuring a density error value representative of the influence of viscosity on the density sensing device,
measuring a viscosity error value representative of the influence of density on the viscosity sensing device,
calculating a corrected density value based upon the measured density value and the measured density error value, and
calculating a corrected viscosity value based upon the measured viscosity value and the measured viscosity error value.

11. A method according to claim 10 further comprising the steps of:

using each of the measured values as a first approximation for a first iterative step,
using the results of the first iterative step as corrected approximations for a second iterative step, and
continuing the iterations until the relative difference between the values obtained by two successive iterative steps is smaller than a pre-determined limit value of accuracy.

12. A method according to claim 11 further comprising the steps of:
measuring the density and the viscosity of a calibration gas of known physical properties,
storing the values obtained by measuring the density and the viscosity of the calibration gas as reference values,
measuring the density and the viscosity of a second gas,
storing the values obtained by measuring the density and the viscosity of the second gas,
calculating the ratio of the density of the second gas to the density of the calibration gas
calculating the ratio of the viscosity of the second gas to the viscosity of the calibration gas
determining a first approximation of a flow coefficient ratio,
making iterative corrections to the flow coefficient ratio using a stored characteristic curve for the density sensing device and the calculated ratios of the density and the viscosity until the relative difference between two successive iterative steps is less than a pre-determined limit value of accuracy.

13. A method according to claim 11 wherein the iteration is commenced with the following initial values: $\rho$ and $\eta$ as previously measured, the initial value of $\eta$ being not yet corrected for the influence of density, and with an initial viscosity-dependent pressure difference equal to an average pressure difference previously determined as a characteristic property of the apparatus used for performing the method claimed herein, and further comprising the steps of calculating a density-dependent first inlet pressure difference by using the equation $$\Delta p_\rho^{(N)} = 2.15 \cdot \frac{\rho}{2} \cdot \frac{\Delta p_\eta^{(N-1)}}{32 \frac{l}{d^2} \cdot \eta^{(N-1)}} \qquad 2$$

where N is equal to the number of iterations, 1 is equal to the length of the capillary tube and d is equal to the diameter of the capillary tube, calculating a viscosity-dependent pressure difference in the capillary tube by using the equation $$\Delta p_\eta^{(N)} = \Delta p - \Delta p_\rho^{(N)}$$

and determining via the equation $$\eta^{(N)} = \eta^{(N-1)} \frac{\Delta p_\eta^{(N)}}{\Delta p_\eta^{(N-1)}}$$

the relative difference $$\frac{\eta^{(N)} - \eta^{(N-1)}}{\eta^{(N)}}$$

and comparing the relative difference with the predetermined limit value of accuracy.

14. An apparatus for the measurement of gas properties comprising:
a gas holding device including a gas holding chamber having a volume that varies in response to pressure differences between the interior of the gas holding chamber and the ambient atmosphere;
a closable gas inlet through which gas is supplied to the gas holding chamber,
at least one turbulent flow restrictor across which gas is discharged from the gas holding chamber,
time measurement means for measuring the period of time taken for the volume of the chamber to decrease from a first predetermined volume representative of a first pressure difference to a second predetermined volume representative of a second pressure difference, and
a laminar flow restrictor, wherein the laminar flow restrictor and the turbulent flow restrictor are connected in parallel and coupled to the gas holding device, the apparatus further including
a gas way for carrying gas discharged from the gas holding device,
an isolating valve associated with the laminar flow restrictor,
controller means for controlling the isolating valves and for successively incorporating the flow restrictors in the gas way carrying gas discharged from the gas holding device.

* * * * *